(12) United States Patent
Popoola et al.

(10) Patent No.: US 8,142,511 B2
(45) Date of Patent: Mar. 27, 2012

(54) BI-MATERIAL PROSTHESIS COMPONENT

(75) Inventors: Oludele O. Popoola, Granger, IN (US);
J. Craig Fryman, New Paris, IN (US);
Ning Yu, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 9 days.

(21) Appl. No.: 12/762,808

(22) Filed: Apr. 19, 2010

(65) Prior Publication Data
US 2011/0257757 A1  Oct. 20, 2011

(51) Int. Cl.
*A61F 2/32* (2006.01)
(52) U.S. Cl. ............... 623/22.17; 623/22.21; 623/19.12; 623/23.4; 623/23.56
(58) Field of Classification Search ............... 623/22.15, 623/22.16, 22.17, 22.18, 23.12, 23.4, 23.42
See application file for complete search history.

(56) References Cited

U.S. PATENT DOCUMENTS

| | | | |
|---|---|---|---|
| 4,034,418 A | 7/1977 | Jackson et al. | |
| 5,021,061 A | 6/1991 | Wevers et al. | |
| 5,037,438 A | 8/1991 | Davidson | |
| 5,171,282 A | 12/1992 | Piquignot | |
| 5,180,394 A | 1/1993 | Davidson | |
| 5,358,529 A | 10/1994 | Davidson | |
| 6,105,235 A | 8/2000 | Caldarise | |
| 6,214,051 B1 | 4/2001 | Badorf et al. | |
| 6,383,222 B1 | 5/2002 | Badorf | |
| 6,447,550 B1 | 9/2002 | Hunter et al. | |
| 6,652,586 B2 | 11/2003 | Hunter et al. | |
| 6,660,040 B2 | 12/2003 | Chan et al. | |
| 6,726,725 B2 | 4/2004 | Hunter et al. | |
| 6,866,685 B2 | 3/2005 | Chan et al. | |
| 2005/0033445 A1* | 2/2005 | Siebel | 623/22.15 |
| 2006/0052875 A1 | 3/2006 | Bernero et al. | |
| 2006/0184251 A1* | 8/2006 | Zhang et al. | 623/23.56 |
| 2007/0107182 A1 | 5/2007 | Sutton | |
| 2008/0188944 A1 | 8/2008 | Ernsberger | |
| 2008/0200988 A1 | 8/2008 | Carroll | |
| 2008/0221680 A1 | 9/2008 | Hodorek | |
| 2008/0228282 A1* | 9/2008 | Brodowski | 623/22.11 |
| 2008/0288081 A1 | 11/2008 | Scrafton et al. | |
| 2009/0125115 A1 | 5/2009 | Popoola et al. | |
| 2009/0171466 A1 | 7/2009 | Frazee et al. | |

* cited by examiner

*Primary Examiner* — Thomas J Sweet
*Assistant Examiner* — Brian Dukert
(74) *Attorney, Agent, or Firm* — Faegre Baker Daniels LLP

(57) ABSTRACT

A prosthesis has prosthetic components principally comprising metallic materials, in which a portion of an articular interface between respective components is a metallic-nonmetallic interface. At least a portion of the articular surface of a femoral head may include a ceramic material defining an articulation zone, such as at a polar region of the femoral head, so that the ceramic articulates with a metallic acetabular liner. The area covered by the ceramic may be engineered to optimize the contact conditions between the femoral head and the acetabular liner, such as by providing two clearances therebetween. A relatively smaller, polar articulation clearance is defined by the gap between the ceramic coating and the metallic acetabular liner. A relatively larger, equatorial non-articulation clearance between the femoral head and the acetabular liner is defined by the gap between the portion of the femoral head not covered by the ceramic coating.

21 Claims, 3 Drawing Sheets

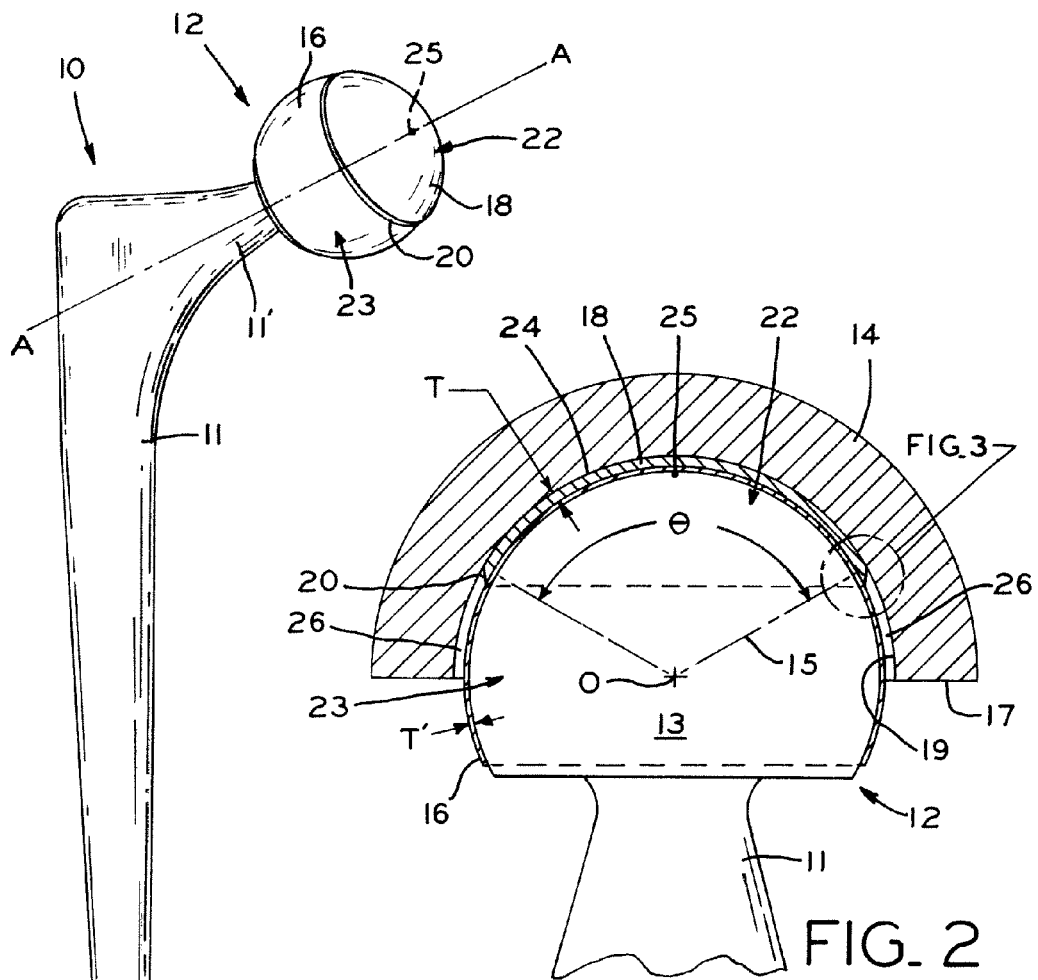
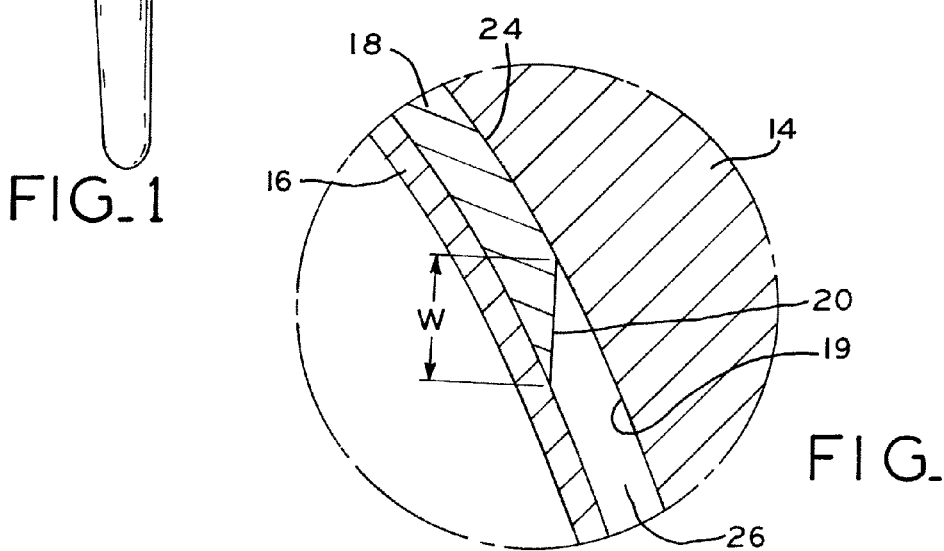
FIG. 1
FIG. 2
FIG. 3

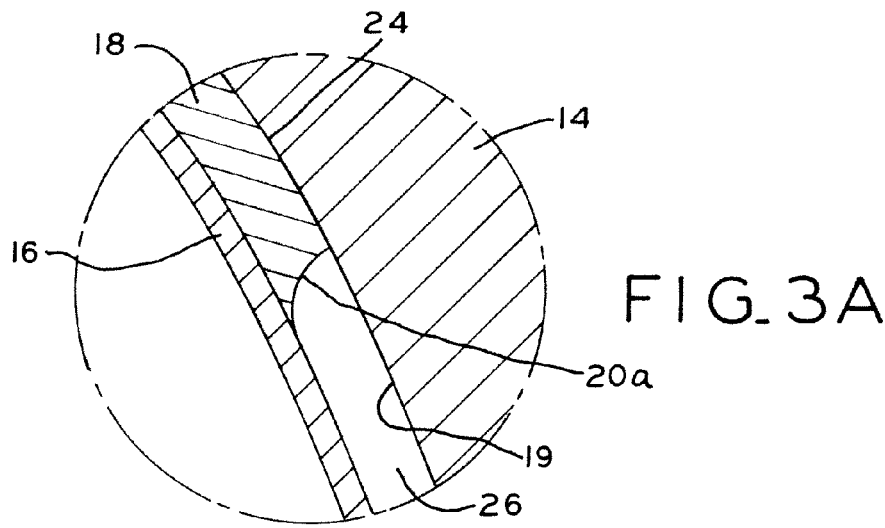
FIG_3A
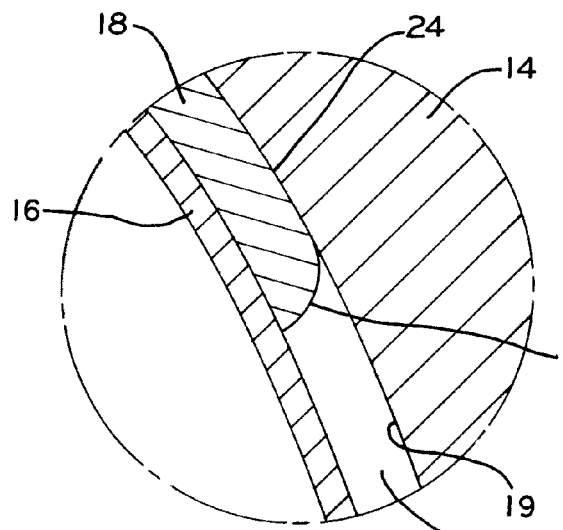
FIG_3B
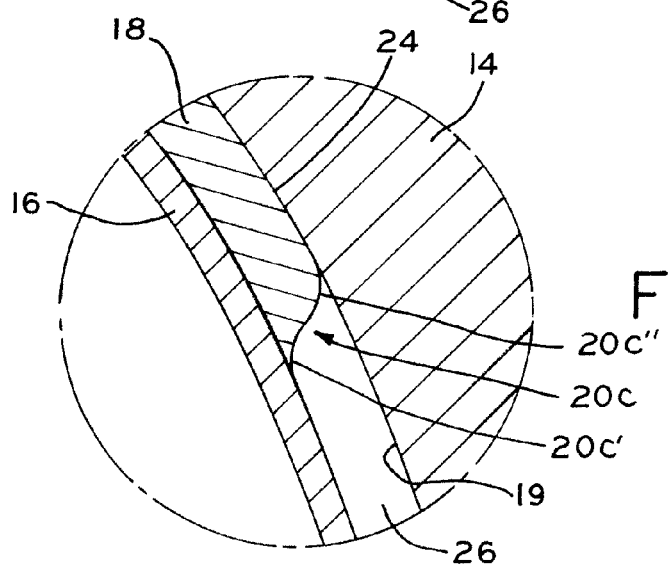
FIG_3C

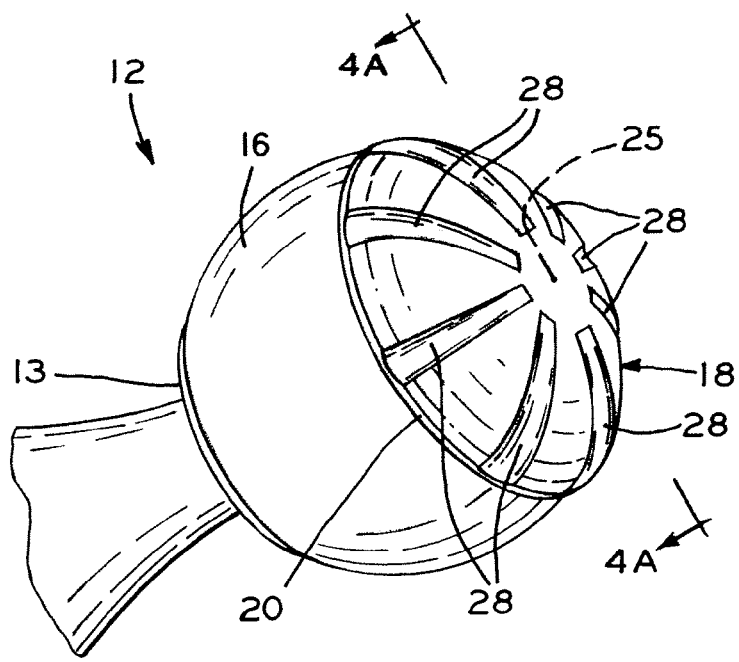
FIG_4
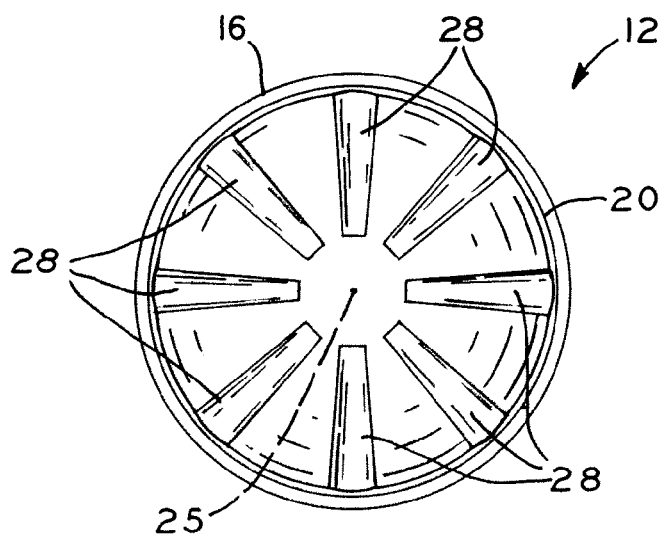
FIG_4A

BI-MATERIAL PROSTHESIS COMPONENT

BACKGROUND

1. Technical Field

The present disclosure relates generally to joint replacement surgery, and more particularly to a prosthesis with a modified articular surface.

2. Brief Description of the Related Art

Joint replacement surgery is used to replace one or more damaged articular joint surfaces or components, thereby allowing the joint to function normally when it would otherwise not be possible to do so. For example, hip arthroplasty is a common joint replacement surgery in which a diseased or damaged femoral head and/or acetabulum is removed and replaced with one or more artificial components. In a typical hip arthroplasty procedure, a femoral component is secured to the femur after resection of the natural femoral head, and a prosthetic femoral head is affixed to the femoral component to approximate the location and orientation of the natural femoral head. The acetabulum of the hip joint may also be resected and replaced with a prosthetic acetabular cup designed to articulate with the prosthetic femoral head. The prosthetic femoral head and acetabular cup may be made of metallic, ceramic and/or polymer components, for example.

Longevity is desirable in the components used in a hip arthroplasty procedure, to reduce or eliminate the need for revision surgery and enhance functionality during the service life of the hip prosthesis. In addition to increasing longevity, minimizing wear of the hip prosthesis components also curtails the potential release of particulate material from prosthetic components into the patient's body. One method of reducing wear in hip prostheses is to select a femoral head component having a different hardness as compared with the acetabular cup component. For example, the acetabular cup may be made of a metallic material and the femoral head may be made of a ceramic material, creating a bearing surface in which respective bearing surface components have disparate material properties, such as hardness (i.e., the relatively softer metallic acetabular cup and the relatively harder ceramic femoral head). These disparate material properties may prolong the service life of the hip prosthesis.

SUMMARY

The present disclosure provides a prosthesis, and a method for making the same, in which the prosthetic components principally comprise metallic materials, but at least a portion of an articular interface between respective components is a metallic-nonmetallic interface. For example, at least a portion of the articular surface of a femoral head may include a ceramic material defining an articulation zone, such as at a polar region of the femoral head, so that the ceramic articulates with a metallic acetabular liner. The area covered by the ceramic may be engineered to optimize the contact conditions between the femoral head and the acetabular liner, such as by providing two clearances therebetween. A relatively smaller, polar articulation clearance is defined by the gap between the ceramic coating and the metallic acetabular liner (i.e., an articulation zone having a ceramic-on-metal interface). A relatively larger, equatorial non-articulation clearance between the femoral head and the acetabular liner is defined by the gap between the portion of the femoral head not covered by the ceramic coating (i.e., an non-articulation zone, which has a ceramic-on-metal or metal-on-metal interface, depending on whether the remainder of the surface of the femoral head is also coated with ceramic).

The geometry of the transition area between the articulation zone and the non-articulation zone can be engineered to optimize lubrication during ambulation. In addition, channels or grooves may be formed in the ceramic of the articulation zone to promote entrainment of lubricating fluid from the non-articulation zone to the articulation zone.

The ceramic area of the femoral head can be produced by various methods, including coatings, coverings, inlays, encapsulation and chemical processes such as oxidation, nitriding, and other processes. A coating or covering may be applied to an unmodified femoral head, or may cooperate with a modified area, such as an indented or surface-treated area, for example, to bond with the femoral head.

In one embodiment, a prosthesis for a ball and socket joint is provided. The prosthesis includes a body having a curved portion, and the body has a polar region with a radial center. The prosthesis further includes a cup with an interior wall defining a concave cavity sized to receive the body, and a coating covering between 60 degrees and 120 degrees of the polar region of the body when viewed in cross-section and measured from the radial center. The coating is disposed between the body and the interior wall of the cup when the body is disposed within the cavity.

In one aspect, the coating may include a transition extending between an outer surface of the coating and an outer surface of the body. The coating may have a thickness between 50 microns and 200 microns.

In another aspect, the coating may be harder than the interior wall of the cup. For example, the coating may be harder by forming the interior wall of the cup from a metallic material and forming the coating from a ceramic material.

In another aspect, with the body disposed within the cavity, a gap may be formed between the body and the interior wall of the cup at a location of the body that is not covered by the coating.

In yet another aspect, the coating may include at least one groove formed in coating, the groove extending from a first location at a junction between the coating and body, across a portion of the coating, to a second location at the junction that is different from the first location.

In still another aspect, the body may be a femoral head and the cup may be an acetabular liner.

In another aspect, the curved portion of the body may be spherical.

In another embodiment, a prosthesis is provided which includes a body with a curved portion, with the body having a polar region with a radial center. The prosthesis also includes a cup with an interior wall defining a concave cavity sized to receive the body in which the interior wall has a first hardness, and a coating disposed on the body, the coating having a thickness of between 50 microns and 200 microns. The coating has a second hardness that is greater than the first hardness.

In one aspect, the coating covers between 60 degrees and 120 degrees of the polar region when viewed in cross-section and measured from the radial center.

In another aspect, the coating may include a transition extending between an outer surface of the coating and an outer surface of the body.

In another aspect, with the body disposed within the cavity, a gap may be formed between the body and the interior wall of the concave cup at a location of the body that is not covered by the coating.

In yet another aspect, the interior wall of the cup may include a metallic material and the coating may include a ceramic material.

In still another aspect, the coating may include at least one groove formed in the coating, the groove extending from a first location at a junction between the coating and body, across a portion of the coating, to a second location at the junction that is different from the first location.

In another aspect, the body may be a femoral head and the cup may be an acetabular liner.

In yet another embodiment, a prosthesis is provided which includes a femoral component adapted to be fixed to a bone, and a femoral head attached to the femoral component. The femoral head includes: a polar region having a first radius, the polar region disposed opposite the femoral component and defining an angular span of between 60 degrees and 120 degrees as viewed in cross-section; an equatorial region having a second radius, the equatorial region disposed between the femoral component and the polar region, so that the first radius is greater than the second radius by at least 50 microns; and a transition region disposed at a junction between the polar region and the equatorial region, the transition region having a width of at least 20 microns. The transition region provides a gradual transition from the first radius to the second radius.

In one aspect, the first radius may be greater than the second radius by less than 200 microns.

In another aspect, the prosthesis may include an acetabular liner with an interior wall defining a concave cavity sized to receive the femoral component, with the interior wall having a first hardness, and the polar region of the femoral component having a second hardness that differs from the first hardness.

In another aspect, at least a portion of the femoral head may be spherical.

In yet another aspect, the polar region may have a surface including a ceramic material, and the equatorial region may have a surface including a metallic material.

In yet another aspect, the polar region includes at least one groove formed therein, the groove extending from the transition region at a first location on the femoral head, across a portion of the polar region, and to the transition region at a second location on the femoral head.

BRIEF DESCRIPTION OF THE DRAWINGS

The above mentioned and other features and advantages of this disclosure, and the manner of attaining them, will become more apparent and the invention itself will be better understood by reference to the following description of an embodiment of the invention taken in conjunction with the accompanying drawings, wherein:

FIG. 1 is a perspective view of a portion of a hip prosthesis, illustrating a femoral component and a femoral head in accordance with the present disclosure;

FIG. 2 is an elevational, sectional view of the femoral head shown in FIG. 1, illustrating coatings on the femoral head;

FIG. 3 is an elevational, sectional view of a portion of the femoral head shown in FIG. 2, illustrating a chamfered transition region;

FIG. 3A is an elevational, sectional view of a portion of the femoral head shown in FIG. 2, illustrating a concave transition region;

FIG. 3B is an elevational, sectional view of a portion of the femoral head shown in FIG. 2, illustrating a convex transition region;

FIG. 3C is an elevational, sectional view of a portion of the femoral head shown in FIG. 2, illustrating a hybrid concave/convex transition region;

FIG. 4 is a partial perspective view of a portion of the hip prosthesis shown in FIG. 1, with an alternative femoral head coating; and FIG. 4A is a top plan view of the portion of the hip prosthesis shown in FIG. 4.

The exemplification set out herein illustrates an exemplary embodiment of the present invention, and such exemplification is not to be construed as limiting the scope of the invention in any manner.

DETAILED DESCRIPTION

Referring to FIG. 1, prosthesis 10 includes femoral component 11 with femoral head 12 attached at a proximal end thereof. Femoral head 12 includes substrate 13 (FIG. 2) including polar region 22 forming a "cap" on femoral head 12 proximate pole 25 (FIG. 2, discussed below) and equatorial region 23 forming an annular "band" disposed between femoral component 11 and polar region 22. Substrate 13 is made of a metallic material, such as titanium, titanium alloys, and other alloys including cobalt chromium and zirconium materials such as cobalt chrome molybdenum, for example. Femoral head 12 also includes polar coating 18 made of a ceramic material, with coating 18 disposed at polar region 22 of femoral head 12. An inner, optional coating 16 may extend over a portion of an outer surface of femoral head 12, such as over more than half of femoral head 12. Polar coating 18 is disposed at polar region 22 of femoral head 12 and extends over less than half of femoral head 12, as discussed below.

As used herein, "coating" refers to a dissimilar material applied to a substrate by any of a variety of methods and modalities. For example, coating 18 may be applied to substrate 13 of femoral head 12 by a coating process in which a flowable or particulate material is deposited on the solid substrate 13, and then cured or solidified in bonding engagement with substrate 13. Coating methods in accordance with the present disclosure include encapsulation and chemical processes such as oxidation, nitriding, and other processes. Alternatively, coating 18 may be deposited on substrate 13 by forming coating 18 separately from substrate 13, i.e., as a covering, and then bonding coating 18 to femoral head 12.

Coating 18 may cover or be deposited on an unmodified substrate 13, as shown in FIG. 2, or coating 18 may be applied to a modified area of substrate 13. For example, femoral head 12 may include a depression or divot formed in substrate 13 sized to receive coating 18, so that coating 18 takes the form of an inlay. The modified area of substrate 13 may also include, for example, a surface treatment differing from the remainder of substrate 13 to promote bonding of coating 18 with substrate 13 of femoral head 12.

Referring now to FIG. 2, femoral head 12 is shaped and sized to articulate with an acetabular cup or liner 14 in the manner of a ball and socket joint. Radius of curvature 15 of femoral head 12 (which originates at a radial center, or origin "O") varies depending on the presence or absence of one or more coatings. For example, radius 15 of femoral head 12 is effectively increased by optional coating 16 (where coating 16 is present) by an amount equal to thickness T' of coating 16. Radius of curvature 15 of femoral head 12 is further increased by thickness T of polar coating 18 in places where polar coating 18 is present.

Optional coating 16 may cover a portion of femoral head 12 that is available for articulation, i.e., a portion of femoral head 12 that may be potentially come in to contact with acetabular liner 14 at the limits of motion of the ball and socket joint. Alternatively, optional coating 16 may cover substantially all of the remaining exposed surfaces of femoral head 12, i.e., the surfaces that are not covered by polar coating 18. In yet another alternative, optional coating 16 may be a surface treatment or process applied to substrate 13 of femoral head 12, so that optional coating 16 provides little or no increase in radius of curvature 15 of femoral head 12.

Acetabular liner 14 includes a concave interior surface with a radius of curvature generally corresponding with the increased radius of curvature created by coatings 16, 18 on femoral head 12. Polar coating 18 defines an articular surface of femoral head 12 when femoral head 12 is received within a cavity defined by concave interior surface 19 of acetabular liner 14. When so received, polar coating 18 engages with concave surface 19 of acetabular liner 14 to define articular interface 24, while uncoated areas at equatorial region 23 of femoral head 12 define a diametrical space or gap 26 between optional coating 16 and acetabular liner 14 or, if optional coating 16 is not present, between substrate 13 and acetabular liner 14. Polar coating 18 may be made of a different material than acetabular liner 14, thereby establishing a bearing surface between polar coating 18 and acetabular liner 14 in which the respective bearing surface components have disparate material properties. For example, and as discussed below, polar coating 18 may be made from a relatively harder ceramic material while acetabular liner 14 may be made from a relatively softer metallic material, which may serve to mitigate wear at articular interface 24. Alternatively, polar coating 18 and liner 14 may be made from the same or similar materials, and may establish different hardnesses for respective bearing components through material treatments such as alloying, heat treatment or the like.

Referring still to FIG. 2, polar coating 18 is generally disposed about polar region 22 of femoral head 12, and extends away from pole 25 of femoral head 12 to define an angular extent θ. In the illustrated embodiment, pole 25 is defined as the point on femoral head 12 furthest from rim 17 of acetabular liner 14 when prosthesis 10 and acetabular liner 14 are oriented so as to correspond to a standing position. In alternative embodiments, pole 25 may be defined as the point on femoral head 12 that is furthest from the interface between substrate 13 and femoral component 11, or may be defined as the point on femoral head 12 intersecting nominal axis A-A (FIG. 1) extending through neck 11' of femoral component 11. Moreover, it is contemplated that pole 25 may defined at any suitable location on femoral head 12, as required or desired for a particular application.

In an exemplary embodiment, polar coating 18 covers polar region 22 of femoral head 12 so that an area of contact at articular interface 24 is optimized for a particular application. For example, polar coating 18 extends downwardly from pole 25 of femoral head 12 to form a "cap" or covering defined by angular extent θ, in which the bottom of the "cap" formed by polar coating is a generally annular structure. As viewed in the cross-sectional plane of FIG. 2, angular extent θ may be as little as 60° or 90°, or as much as 120° (measured as the included angle, as viewed in section, between the two sides extending from radius center O to the end of coating 18), or any value within any range defined by any of the foregoing values. Put another way, the coverage of polar coating 18 may be expressed as a percentage of an overall surface area of femoral head 12. If femoral head 12 is spherical, this percentage P can be approximated by the following formula:

$$P = \frac{1 - \cos\theta}{4} \times 100.$$

Thus, if angular extent θ is between about 60° and about 120°, the percentage of femoral head 12 covered by polar coating 18 is between about 12.5% and 37.5%. However, it will be understood that a typical femoral head is not a complete sphere, so that the actual percentage of polar coating coverage may be somewhat larger. Moreover, the varying of angular extent θ and/or percentage P ensures that the area of contact defined by articular interface 24 is optimized so that the area is small enough to minimize wear and any concomitant potential release of particulate material into the body of the patient, but is large enough to distribute forces experienced at articular interface 24 during joint articulation.

Polar coating 18 defines thickness T (FIG. 2), which may be varied to optimize wear characteristics and force translation between components of femoral head 12. In an exemplary embodiment, thickness T may be as little as 10 microns or 50 microns, and as much as 200 microns or 500 microns, or may be any value within any range defined by any of the foregoing values. Thickness T of polar coating 18 ultimately determines radius of curvature 15 of femoral head 12 at articular interface 24, as discussed above. Therefore, for any given radius of concave internal surface 19 of acetabular liner 14, thickness T is one variable that determines a clearance between femoral head 12 and concave internal surface 19 of acetabular liner 14 at articular interface 24. Variation of thickness T of polar coating 18 can be used to ensure an optimal tightness of fit between femoral head 12 and acetabular liner 14 at articular interface 24, thereby promoting precise articular movement and high joint stability, while also leaving sufficient clearance to minimize the risk of seizure between femoral head 12 and acetabular liner 14. Further, and as discussed in more detail below, thickness T can also be varied to optimize the entrainment of lubrication and/or synovial fluid at articular interface 24.

Polar coating 18 provides two distinct clearances between femoral head 12 and acetabular liner 14. While the articulation clearance at articular interface 24 may be relatively small, as discussed above, the diametrical clearance at gap 26 is comparatively large. Gap 26 is disposed generally opposite polar coating 18 on femoral head 12, so that gap 26 is spaced away from pole 25 and occupies the portion of femoral head 12 that is not covered by polar coating 18 (i.e., equatorial region 23). In an exemplary embodiment, a ratio of the articulation clearance at articular interface 24 to the diametrical clearance at gap 26 is between about 0.1 and about 1.0, or any value between these two ratios. That is to say, gap 26 may be small enough to render the diametrical clearance approximately equal to the articulation clearance, or gap 26 may be large enough to render the diametrical clearance approximately ten times larger than the articulation clearance.

Advantageously, lubricating fluid may be present in relatively large amounts in gap 26, which may promote entrainment of the lubricating fluid into articular interface 24 during articulating movement of prosthesis 10 with respect to acetabular liner 14, as discussed in more detail below. Also advantageously, the larger clearance created by gap 26 near rim 17 of acetabular liner 14 results in a minimized risk of acetabular liner 14 "clamping" on femoral head 12, i.e., becoming fixedly coupled to femoral head 12 so that movement of prosthesis 10 urges a corresponding movement of acetabular liner 14.

Polar coating 18 may include transitional chamfer 20 (FIGS. 2 and 3) extending around the perimeter of the terminus of polar coating 18. Transitional chamfer 20 provides a smooth transition at the junction between polar coating 18 and substrate 13 (or between polar coating 18 and optional coating 16, if present). Transitional chamfer 20 thus prevents or reduces any "step" or ledge that may be present between a relatively larger radius 15 (such as where femoral head 12 includes thickness T of polar coating 18) and a relatively smaller radius 15 of femoral head 12 (such as where polar coating 18 is absent). This smooth transition enhances formation of a film of lubricating fluid at articular interface 24 by facilitating fluid flow from gap 26 to articular interface 24. As shown in FIG. 3, chamfer 20 has width W defined as the shortest distance along chamfer 20 between polar coating 18 and optional coating 16 (or, where optional coating 16 is not present, between polar coating 18 and substrate 13 of femoral head 12). A larger width W provides a more gradual transition angle between polar coating 18 and optional coating 16 (or substrate 13 of femoral head 12), while a smaller width W provides a sharper, less gradual transition angle. In exemplary embodiments, width W may be as little as 40% of thickness T of coating 18 and as much as 60% of thickness T of coating 18, or any value within this range. For example, where coating 18 has thickness T equal to 50 microns, width W may be between 20 and 30 microns. Similarly, for a where coating 18 has thickness T equal to 200 microns, width W may be between 80 and 120 microns.

In an exemplary embodiment, the transition angle and geometrical configuration of chamfer 20 may be optimized to promote favorable lubricant entrainment into articular interface 24. For example, polar coating 18 and chamfer 20 may be made asymmetrical with respect to polar region 22 by extending chamfer 20 further from pole 25 along some portions of a circumferential extent of chamfer 20 as compared with other portions. This asymmetry of chamfer 20 may provide directionality to lubricating fluid by promoting entrainment of fluid into certain areas of polar region 22 during movement of femoral head 12 relative to acetabular liner 14. For example, in one exemplary embodiment (not shown), coating 18 may have a generally oval profile with the major axis of the oval corresponding to a flexion and extension movement path. Chamfer 20 may also be symmetrical about polar region 22 to allow even fluid entrainment throughout polar coating 18, such as by defining a fixed distance of chamfer 20 from pole 25 around the entire circumferential extent.

Referring now to FIGS. 3A-3C, the geometry of the junction between polar coating 18 and femoral head 13 (or between polar coating 18 and optional coating 16, if present) may take alternative forms to the planar illustration of transitional chamfer 20. For example, concave transition 20a may be provided, as shown in FIG. 3A. Another alternative is convex transition 20b, as shown in FIG. 3B. Yet another alternative is hybrid transition 20c, including both concave portion 20c' and convex portion 20c''. These alternative transition geometries may be used to enhance or modify the entrainment characteristics of fluid from gap 26 to articular interface 24, for example.

Optionally, grooves or channels may be provided in polar coating 18 to aid in the introduction of lubricating fluid to articular interface 24. In the illustrated embodiment of FIGS. 4 and 4A, eight equally-spaced grooves 28 extend across a portion of polar coating 18 to provide a plurality of pathways for lubricating fluid, such as synovial fluid, to travel from gap 26 (FIG. 2) to various portions of articular interface 24 (FIG. 2). Each of grooves 28 extends from chamfer 20 at a first location on femoral head 12, and across a portion of polar coating 18. In the illustrated embodiment, grooves 28 all extend upwardly toward pole 25 of substrate 13 of femoral head 12, while leaving the portion of polar coating 18 near pole 25 intact. Thus, grooves 28 present an unobstructed pathway for fluid to migrate from gap 26 to articular interface 24. More particularly, fluid that enters a respective groove 28 can travel along the extent of the groove 28 to convey lubricating fluid from gap 26 toward pole 25.

In an exemplary embodiment, grooves 28 extend partially into, but not through, polar coating 18. For example, grooves 28 may define a radiused or arcuate cross-sectional profile extending into polar coating 18 by about 40-60% of thickness T. In addition, grooves 28 may vary in width. In the illustrated embodiment of FIG. 4A, for example, each of grooves 28 defines a maximum width at chamfer 20, and tapers to a minimum width near pole 25.

However, it is contemplated that the number, cross-sectional profile and geometrical arrangement of grooves 28 on polar coating 18 may be varied as desired or required for a particular application. For example, grooves 28 may extend entirely across a portion of femoral head, i.e., from chamfer 20 at a first location, across a portion of polar coating 18, and back to chamfer 20 at a second location. Grooves 28 may also be in fluid communication with one another, i.e., by a connecting groove or by overlapping portions of grooves 28. Moreover, grooves 28 may be take any number of forms in order to provide a desired amount and profile of fluid entrainment from gap 26 to articular interface 24.

In the case of an asymmetrical perimeter of chamfer 20, it is contemplated that femoral head 12 may include a structure (not shown) to ensure a proper rotational orientation of femoral head 12 on femoral component 11. This structure may be a key or keyway extending from or formed in femoral head 12, for example, which corresponds with a keyway or key formed in or extending from femoral component 11 to ensure that chamfer 20 is properly oriented. Advantageously, chamfer 20 provides a ramped surface or entrance plane for lubrication fluid, and increases the entrainment velocity thereof to promote entrainment of lubricating fluid throughout articular interface 24.

Advantageously, femoral head 12 with polar coating 18 allows for an optimal area of contact between dissimilar materials (defined by articular interface 24) while retaining the ability to use a relatively large femoral head. A large femoral head offers certain advantages over a smaller counterpart, such as improved range of motion and reduced likelihood of dislocation. With the area of articular interface 24 optimized via polar coating 18, the benefits derived from the use of a large femoral head (i.e., a femoral head having a diameter of 22 mm to 60 mm or larger) are retained while wear between femoral head 12 and acetabular liner 14 is reduced.

Also advantageously, femoral head 12 has improved strength, in that metal substrate 13 of femoral head 12 (FIG. 2) is resistant to fracture. Thus, femoral head 12 has strength characteristics consistent with an entirely metallic femoral head, as well as the desirable wear characteristics of a ceramic femoral head.

In an exemplary embodiment, polar coating 18 and optional coating 16 are made of a ceramic material, while substrate 13 of femoral head 12 and acetabular liner 14 are made of a metallic material. Coatings 16, 18 may minimize patient exposure to the metallic substrate 13. However, it is within the scope of the present disclosure that other materials may be used for optional coating 16 and/or polar coating 18, such as alumina, or non-ceramic materials such as nitrides and metallic compounds, and that coating 16 may be eliminated entirely. It is also contemplated that one or more coatings may be placed on the interior surface of the acetabular liner, rather than on the femoral head. Further, although the illustrated embodiment discloses a spherical or spheroidal articular surface, it is contemplated that other surface geometries may be used. For example, the coated outer surface of substrate 13 and/or the surface of the polar coating 18 itself may be conicoidal, or may have any complex curved surface.

It is further contemplated that coatings in accordance with the present disclosure may also be used in other contexts, such as for glenoid prostheses or in other anatomical surfaces. Such coatings may also be used in the context of non-ball and socket joints, such as in knee prostheses for articulation between the tibia and femur or femur and patella, for example. Moreover, such coatings may be used in any context in which disparate material properties, such as differing hardnesses, are required or desired, or in which it is desired or required to define an articular surface with less than the entire available surface area of the surface.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthesis for a ball and socket joint, the prosthesis comprising:
   a body having a curved portion, said body having a polar region with a radial center;
   a cup prosthesis having an exterior wall, and an interior wall defining a concave cavity sized to receive said body;
   a coating integral with said body and covering only between 60 degrees and 120 degrees of said polar region of said body when viewed in cross-section and measured from said radial center, said coating disposed between said body and said interior wall of said cup prosthesis with an articular interface defined between said coating and said interior wall of said cup prosthesis when said body is disposed within said cavity.

2. The prosthesis of claim 1, wherein said coating further comprises a transition extending between an outer surface of said coating and an outer surface of said body.

3. The prosthesis of claim 1, wherein said coating has a thickness between 50 microns and 200 microns.

4. The prosthesis of claim 1, wherein said coating is harder than said interior wall of said cup.

5. The prosthesis of claim 4, wherein said interior wall of said cup comprises a metallic material and said coating comprises a ceramic material.

6. The prosthesis of claim 1, wherein, with said body disposed within said concave cavity, a gap is formed between said body and said interior wall of said cup at a location of said body not covered by said coating.

7. The prosthesis of claim 1, wherein said coating comprises at least one groove formed in said coating, said groove extending from a junction between said coating and said body, and across a portion of said coating toward a pole of said polar region.

8. The prosthesis of claim 1, wherein said body comprises a femoral head and said cup comprises an acetabular liner.

9. A prosthesis comprising:
   a body having a curved portion, said body having a polar region with a radial center;
   a cup prosthesis having an exterior wall, and an interior wall defining a concave cavity sized to receive said body, said interior wall having a first hardness;
   a coating integral with said body disposed on said body covering only between 60 degrees and 120 degrees of said polar region of said body when viewed in cross-section and measured from said radial center, said coating having a thickness of between 50 microns and 200 microns, said coating having a second hardness that is greater than said first hardness.

10. The prosthesis of claim 9, wherein said coating covers between 60 degrees and 120 degrees of said polar region when viewed in cross-section and measured from said radial center.

11. The prosthesis of claim 9, wherein said coating further comprises a transition extending between an outer surface of said coating and an outer surface of said body.

12. The prosthesis of claim 9, wherein, with said body disposed within said concave cavity, a gap is formed between said body and said interior wall of said cup at a location of said body not covered by said coating.

13. The prosthesis of claim 9, wherein said interior wall of said cup comprises a metallic material and said coating comprises a ceramic material.

14. The prosthesis of claim 9, wherein said coating comprises at least one groove formed in said coating, said groove extending from a junction between said coating and said body, and across a portion of said coating toward a pole of said polar region.

15. The prosthesis of claim 9, wherein said body comprises a femoral head and said cup comprises an acetabular liner.

16. A prosthesis comprising:
   a femoral component adapted to be fixed to a bone;
   a femoral head attached to said femoral component, said femoral head comprising:
      a polar region integral with the femoral head having a first radius, said polar region disposed opposite said femoral component and defining an angular span of between only 60 degrees and 120 degrees as viewed in cross-section;
      an equatorial region having a second radius, said equatorial region disposed between said femoral component and said polar region, and said first radius is greater than said second radius by at least 50 microns; and
      a transition region disposed at a junction between said polar region and said equatorial region, said transition region having a width of at least 20 microns, whereby said transition region provides a gradual transition from said first radius to said second radius.

17. The prosthesis of claim 16, wherein said first radius is greater than said second radius by less than 200 microns.

18. The prosthesis of claim 16, further comprising an acetabular liner with an interior wall defining a concave cavity sized to receive said femoral head, said interior wall having a first hardness, and said polar region of said femoral head having a second hardness that differs from said first hardness.

19. The prosthesis of claim 16, wherein at least a portion of said femoral head is spherical.

20. The prosthesis of claim 16, wherein said polar region has a surface comprising a ceramic material, and said equatorial region has a surface comprising a metallic material.

21. The prosthesis of claim 16, wherein said polar region includes at least one groove formed therein, said groove extending from said transition region, and across a portion of said polar region toward a pole of said polar region.

* * * * *